(12) United States Patent
Bishop et al.

(10) Patent No.: US 7,524,504 B1
(45) Date of Patent: Apr. 28, 2009

(54) **ANTI-GLYCATION HYDROLYSATE OF *G. LUCIDUM***

(76) Inventors: Michael Bishop, 9400 Rockbrook Dr., Dallas, TX (US) 75220; Elysiann Bishop, 9400 Rockbrook Dr., Dallas, TX (US) 75220; Walter Smith, 3677 Touch of Class Court, Wellington, FL (US) 33414; Glen Gillis, 3609 Montecito Dr., Denton, TX (US) 76205

( * ) Notice: Subject to any disclaimer, the term of this patent is extended or adjusted under 35 U.S.C. 154(b) by 0 days.

(21) Appl. No.: 12/007,655

(22) Filed: Jan. 14, 2008

(51) Int. Cl.
*A61K 35/84* (2006.01)
(52) U.S. Cl. .................................. 424/195.15
(58) Field of Classification Search ....................... None
See application file for complete search history.

(56) References Cited

U.S. PATENT DOCUMENTS

| | | | | |
|---|---|---|---|---|
| 5,173,403 | A | * 12/1992 | Tang et al. | ...... 435/6 |
| 6,395,310 | B1 | * 5/2002 | Iwasaki | ...... 424/725 |
| 2006/0045894 | A1 | * 3/2006 | Brown et al. | ...... 424/401 |
| 2007/0160563 | A1 | * 7/2007 | Bishop et al. | ...... 424/74 |

FOREIGN PATENT DOCUMENTS

| | | | |
|---|---|---|---|
| CN | 101085108 | * | 12/2007 |
| CN | 101176548 | * | 5/2008 |

* cited by examiner

*Primary Examiner*—Christopher R. Tate
(74) *Attorney, Agent, or Firm*—Louis C. Paul

(57) ABSTRACT

Methods and compositions for reducing the levels of Advanced Glycation Endproducts (AGE) related proteins in the skin by topical application of dermatocosmetic compositions comprising effective amounts of extracts of *Ganoderma lucidum* that have been hydrolyzed by an acid protease, preferably *Rhizomucor miehei*, and thereafter rendered substantially devoid of acid-protease activity.

10 Claims, No Drawings

ANTI-GLYCATION HYDROLYSATE OF G. LUCIDUM

FIELD OF INVENTION

The present invention relates to topical compositions that reduce the appearance of fine lines wrinkles and other signs associated with chronological or environmental aging. More particularly, the present invention is directed to methods and compositions for reducing the levels of Advanced Glycation Endproducts (AGE) related proteins in the skin by topical application of dermatocosmetic compositions comprising effective amounts of extracts of *Ganoderma lucidum* that have been hydrolyzed by an acid protease, preferably *Rhizomucor miehei*, and thereafter rendered substantially devoid of acid-protease activity.

STATEMENT OF FEDERALLY-SPONSORED RESEARCH

Not applicable.

BACKGROUND OF THE INVENTION

Glycation is a physiologic process that has been implicated in aging. More specifically, it is a non-enzymatic reaction between reducing sugars and the free amino acid groups of proteins, ultimately producing AGE related proteins such as carboxymethyllysine, pentosidine and methyl glyoxal-lysine dimer. In addition to being implicated in a number of diseases, including diabetes, AGE related proteins have associated with skin aging, including progressive changes characterized by decreased tensile strength, increased resistance to enzymatic digestion and increased non-enzymatic cross-links (Pageon et al). Methyl glyoxal and other reactive carbonyl species have also been implicated in disruption of melanocyte (Wondrak et al) and mitochondrial function (Rosca et al) See also, S. Daniel et al., "Collagen glycation and skin aging" accessed on Aug. 8, 2007 at www.mibellebiochemistry.com/pdfs/Collagen_glycation_and_skin_aging_-_CT_2002.pdf.

Mechanistically, methylglyoxal reacts with amino acid residues of proteins, in particular arginyl residues, forming AGE related proteins. G S Gillis, Selwood et al, Takahash et al, Cheung et al., Riley et al, Ahmed et al, Aboro et al, Westwood et al. The glyoxalase system mediates the conversion of the α-ketoaldehyde methylglyoxal to a hydroxyacid. More specifically, the glyoxalase system is composed of two enzymes, glyoxalase I (E.C. 4.4.1.5, lactoylglutathione lyase) (Glo-I) and glyoxalase II (E.C. 3.1.2.6, hydroxyacylglutathione hydrolyase) (Glo-II) and requires a catalytic quantity of reduced glutathione (GSH). In a first non-enzymatic reaction, the Glo-I hemithioacetal is formed from α-ketoaldehyde and reduced GSH. In a second reaction, Glo-I is isomerized to α-D-hydroxyacid thioester which then undergoes enzymatic hydrolysis in the presence of a Glo-II catalyst to α-D-hydroxyacid. Reduced GSH is recycled in the reaction.

Studies report a positive correlation between the amount of AGE in human skin and increasing age. As measured by collagen-linked fluorescence, AGE levels increase at a rate of about 3.7% per year. Skin auto-fluorescence has been correlated with the increased presence of specific AGE. For example, carboxymethyl lysine and pentosidine have been shown to increase five-fold between the ages of 20 and 85.

Surprisingly and unexpectedly, extracts of Reishi mushroom hydrolyzed by an acid protease of *Rhizomucor miehei* and then rendered substantially devoid of acid-protease activity have been found to upregulate expressions of genes that code for Glo-I. Without wishing to be bound by a theory, applicants believe that by increasing the levels of Glo-I, the levels of α-ketoaldehydes—including, in particular, methylglyoxal—are reduced, thereby decreasing the formation of AGE related protein in mammals.

The Reishi mushroom (*Ganoderma lucidum*), also known as Red Reishi, Ling Zhi (in China), Yeong Ji (in Korea), has long been used traditional medicine of Asian cultures. See, e.g., S. Aung, "The Clinical Use of Mushrooms from a Traditional Chinese Medical Perspective" *International Journal of Medicinal Mushrooms*," Vol. 7, No. 3, pp. 375-376 (2005); P. Poucheret et al. "Biological and Pharmacological Activity of Higher Fungi: 20-Year Retrospective Analysis" *Cryptogamie Mycologie*, Vol. 27, No. 4, pp. 311-333 (2006).

Reishi has been used an ingredient in oral nutritional supplements. See, e.g., U.S. Patent Application Publication 2003/0008048 teaching a dietary nutritional supplement for helping the body resist the effects of the aging process comprising: (i) at least one of Vitamin c, schisandra berry, raspberry, strawberry, pomegranate, and elderberry; (ii) bilberry or blueberry; (iii) green tea or dark chocolate; (iv) mixed carotenoids, echinacea, or goldenseal; (v) tocopherols, tocotrienols, zinc, or selenium; (vi) Coenzyme Q10; and (vii) reishi mushroom extract.

The use of Reishi in orally-administered medicinal formulations is further described in the patent literature. See, e.g., U.S. Pat. No. 6,541,0431 (treatment of Attention Deficit/Hyperactivity Disorder with a composition containing reishi in combination with Vitamins (A, $B_5$, $B_6$, $B_{12}$, C and E), reishi, lecithin, choline, 5-hydroxytryptophan and/or tyrosine).

It is known to those of skill in the art that using different solvents can produce different extracts, with different biological activities. In the case of Reishi, an alkali-extracted peptidoglycan from Korean *Ganoderma lucidum* is reported to be different in chemical composition than a water-based extract of the same plant. The alkali-based extract was reported to contain 6.9% protein and 75.9% carbohydrates (primarily glucose and mannose), with the polysaccharides covalently bound to a polypeptide core. J Y Cheong et al., "Characterization of Alkali-extracted Peptidoglycan from Korean *Ganoderma lucidum* "*Arch. Pharm. Res*. Vol. 22, No. 5, pp. 515-519 (1999). The biological activity of the alkali extract is not reported in the Cheong (1999) reference.

An ethanol-extract of the mycelium of *Ganoderma lucidum* indigenous to the southern part of the Indian subcontinent has been reported to have topical anti-inflammatory effects in animals. See, B. Lakshmi et al., "Antiperoxidative, anti-inflammatory, and antimutagenic activities of ethanol extract of the mycelium of *Ganoderma lucidum* occurring in South India" *Teratog. Carcinog. Mutagen*. Vol. 23, Suppl. 1, pp. 85-97 (2003) (intraperitoneal administration of extract reduced inflammation and edema in mice).

U.S. Patent Application Publication No. 2003/0095981 teaches a process for preparing a biologically-active fraction of *Ganoderma lucidum* having an optical absorbance of from about 200 nm to about 280 nm and use of the active fraction in treating rheumatoid arthritis and osteoarthritis.

The antioxidant and immunomodulatory effects of orally-ingested *Ganoderma lucidum* have been reported in the scientific literature. See, e.g., J M Lin et al. "Radical scavenger and antihepatotoxic activty of *Ganoderma formosanum, Ganoderma lucidum* and *Ganoderma japonicum*" *Journal of Ethnopharmacology* Vol. 47, No. 1, pp. 33-41 (1995); Z B Lin "Anti-tumor and immunoregulatory activities of *Ganoderma lucidum* and its possible mechanisms" *Acta. Pharmacol. Sin*. Vol. 25, No. 11, pp. 1387-95 (November 2004).

Reishi extract has been used in topically-applied skincare products. Origins Plantidote™ Mega-Mushroom Face Serum comprises Reishi in combination with two other mushrooms (*Hypsizygus ulmarius* (elm oyster) and *Cordyceps sinensis*) and Reishi. Estée Lauder Re-Nutriv Revitalizing Comfort Créme contains Reishi in combination with wolfberry and ginseng.

Active Concepts (South Plainfield, N.J.) sells a fermented combination of Reishi and Shiitake Mushrooms under the tradename ACB Mushroom Extract SM (INCI name *Lactobacillus/Ganoderma Lucidum* (Reishi Mushroom) Extract/ *Lentinus Edodes* (Shiitake Mushroom) Extract Ferment Filtrate). According to a Technical Data Sheet ("TDS"), twice-daily application of a quick-break emulsion containing the fermented Reishi/Shiitake complex at a concentration of 5% increased skin hydration and firmness. The same TDS reported increased skin cell turnover from an aqueous solution containing 10% ACB Mushroom Extract SM.

U.S. Patent Application Publication No. 2006/0045894 teaches the use of ACB Mushroom Extract SM in a topically-applied product for reducing sagging or wrinkles in the neck of humans comprising capsaicinoid at stimulates increased localized circulation in the skin. At Paragraph [0031], the mushroom complex is taught to be an optional ingredient, at use concentrations of from 0.05% to 10%.

Arch Personal Care (South Plainfield, N.J.) also sells a combination of Reishi and Shiitake Mushrooms under the tradename NAB® Mushroom Extract (INCI Name Algae Extract & *Lentinus Edodes* Extract & *Ganoderma Lucidum* (Reishi Mushroom) Stem Extract). According to the technical information from Arch, skin firmness and hydration were observed to improve after twelve weeks of twice-daily application of a cream containing NAB® Mushroom Extract at a 5% concentration. The Arch TDS likewise reported an increase in skin cell turnover from an aqueous solution containing 10% NAB® Mushroom Extract.

U.S. Pat. No. 7,060,286 teaches topical use of lipids extracted from broken spores of *Ganoderma lucidum* extracted by a supercritical fluid-carbon dioxide. Claimed uses of the lipid spores are reduction in wrinkles and pigment lightening.

Japanese Patent Application JP4009325 entitled "Beautifying and Whitening Cosmetic" teaches the use of an extract of *Ganoderma lucidum* with one or more of ascorbic acid, retinol, pyridoxine, pantothenic acid, and tocopherol.

U.S. Patent Application Publication No. 2006/0029686 (assigned to Access Business Group) teaches administration rosehips and at least one of blackberry, blueberry, resveratrol, and extract of *Aframomum melegueta* to mediate the physiological response caused by interleukin cytokines, specifically inflammation. Primarily directed at oral administration of nutritional supplements containing the above-listed active ingredients, the '686 application teaches compositions additionally containing Reishi.

U.S. Patent Application Publication No. 2005/0158258 (assigned to Mary Kay) teaches topical compositions for treating damaged skin comprising (i) ximenynic acid, a conjugated, unsaturated fatty acid found in sandalwood seeds and (ii) niacin, alpha-lipoic acid, or a mushroom extract. Among the disclosed mushroom extracts is Reishi.

U.S. Patent Application Publication No. 2004/0057917 teaches topical compositions useful in the treatment of photodamaged skin. The disclosed compositions comprise a pharmaceutically-effective amount of an extract of nopal cactus in combination with an anti-inflammatory agent selected from a group including Reishi.

U.S. Patent Application Publication No. 2005/0137239 (assigned to Avon) teaches topical administration of thiazole derivatives to inhibit the formation of advanced glycation endproducts, break advanced glycation endproduct-associated crosslinks, and inhibit glucose oxidase.

U.S. Patent Application Publication No. 2002/0042438 (assigned to L'Oréal) discloses a method for reducing or inhibiting the glycation of skin proteins by topically applying a composition containing ergothioneine and derivatives thereof.

U.S. Patent Application Publication No. 2006/0045896 (assigned to Tracie Martyn Intl) teaches a method for inhibiting glycation of skin proteins and formation of AGE related proteins by topical application of a composition comprising benfotiamine and pyridoxamine.

U.S. Pat. No. 7,005,148 (assigned to L'Oréal) teaches reducing or inhibiting glycation of skin proteins by topical administration of a composition comprising an extract of a *Vaccinium*-type plant.

U.S. Pat. No. 6,414,038 (assigned to L'Oréal) teaches the use of topical compositions comprising a hydroxystilbene compound to reduce or inhibit the glycation of proteins of the skin, the nails and the hair.

A series of related patents assigned to Active Organics, LP—U.S. Pat. Nos. 5,976,556; 6,569,437; and 6,656,701— describe the uses of one or more acid protease enzymes in combination with an acidic buffering system that enhances epidermal exfoliation and/or epidermal cell renewal, thereby improving the texture or appearance of the skin.

Extracts of *Rhizomucor miehei* are commercially-available from a number of sources including and Novozymes Inc. and Active Organics LP (Lewisville, Tex.) exhibit enzymatic activity, principally from-acid proteases.

U.S. Patent Application Publication No. 2007/0160563 discloses topical compositions comprising extracts of *R. miehei* that are substantially devoid of acid-protease activity and their use in treating dermatologic conditions, including reducing the appearance of signs of skin aging.

There has been and remains a need for compositions and methods for reducing or inhibiting the formation of AGE related proteins. The compositions and methods of the present invention—topical application of an effective amount of an extract of reishi mushroom that has been hydrolyzed by an acid protease and thereafter rendered substantially devoid of acid-protease activity—meet this need.

SUMMARY OF THE INVENTION

The present invention relates to an acid protease hydrolyzed polysaccharopeptide extract of *Ganoderma lucidum* that is substantially devoid of acid protease activity and uses of this hydrolysate to reduce the levels of Advanced Glycation Endproducts (AGE) related proteins as measured in vitro (by reduction in the level of expression of the GLO-1 gene as analyzed using DNA microarrays) and in vivo.

DETAILED DESCRIPTION OF THE INVENTION

Acid protease hydrolyzed polysaccharopeptide extract of *G. lucidum* that is substantially devoid of acid protease activity is commercially-available from the Active Organics LP under the tradename ACTIAGE™ and is produced as follows: An initial fraction of *G. lucidum* is produced by mixing the macerated fruiting body of the mushroom in ethanol at a ratio of from about 1:5 to about 1:3, preferably about 1:4, for a period of from about 36 hours to about 60 hours, preferably for a period of about 48 hours. The resulting precipitate is collected and mixed with an acidic aqueous solvent, having a pH of from about 3.5 to 4.5, preferably from about 3.8 to about 4.2. The acidic aqueous solvent is made by mixing (i) citric acid (3%) and (ii) glycerin or a lower glycol, preferably propylene glycol or butylene glycol (10%) with (iii) deionized water and adjusting the pH to the desired range with a 25% solution of sodium hydroxide.

Preferably, the precipitate is present in the acidic aqueous solvent in a ratio of from about 1:50 to about 1:9, more preferably from about 1:40 to about 1:20. Deionized water is added QS. This precipitate is further extracted for period of from about 36 hours to about 60 hours, preferably for a period of about 48 hours, at a temperature of from about 30° C. to 50° C., more from about 35° C. to about 45° C.

Following this extraction period, the water-soluble polysaccharopeptide proteinaceous fraction is hydrolyzed by addition of an acid protease, preferably an acid protease of *R. miehei*, still more preferably an acid protease of *R. miehei* having from 4,000 to about 10,000 HUT units of activity per milliliter. A preferred acid protease of *R. miehei* is available under the tradename Actizyme® 3M-M from Active Organics LP. The acid protease is added as solution of from about 0.001% to 10%, preferably from about 0.01% to about 3% and more preferably from about 0.5% to about 1.5%. Hydrolysis is then conducted at a temperature of from about 35° C. to about 45° C., preferably at about 40° C., for a period of from about 36 hours to about 60 hours, preferably for a period of about 48 hours. Following hydrolysis, the acid protease is removed or inactivated by techniques well-known to those having ordinary skill in the art, including by molecular weight sieve, thermal inactivation and/or pepstatin-affinity gel chromatography.

According to one aspect of the present invention, the acid protease hydrolyzed polysaccharopeptide extract of *G. lucidum* that is substantially devoid of acid protease activity is present in a dermatologically-acceptable carrier at a concentration of from about 0.01% to about 50%, preferably at a concentration of from about 0.1% to about 10%, still more preferably at a concentration of from about 0.25% to about 5%.

One preferred aspect of the present invention is directed to anti-aging products comprising the acid protease hydrolyzed polysaccharopeptide extract of *G. lucidum* that is substantially devoid of acid protease activity at a concentration of at least about 0.1%. By anti-aging products are meant topical formulations that help reduce the appearance of fine lines, wrinkles, pigment discoloration associated with chronological or environmental aging.

In a particularly preferred aspect of the present invention is directed to anti-aging products comprising the acid protease hydrolyzed polysaccharopeptide extract of *G. lucidum* that is substantially devoid of acid protease activity that reduces the levels of Advanced Glycation Endproducts (AGE) related proteins, thereby creating the appearance of more youthful and healthy skin.

In Vitro Anti-Inflammatory Activity—DNA Microarray Analysis

The anti-inflammatory effect of acid protease hydrolyzed polysaccharopeptide extract of *G. lucidum* that is substantially devoid of acid protease activity is measured based on changes in the level of expression of the GLO-1 gene analyzed using DNA microarrays as described below.

Epidermal full-thickness tissue, supplied by MATEK Corporation, (Ashland, Mass.) is used for in vitro testing. Tissue samples are removed from the shipping tray, placed into a 6-well plate containing 2.5-5.0 ml of assay medium (37±2° C.), and incubated for at least 24 hours at 37±2° C. and 5±1% $CO_2$. After this initial incubation, the assay medium is replaced with 2.5-5.0 ml of fresh medium (37±2° C.). 25-50 ml of test material (test sample) and/or phosphate buffered saline (negative control) is then applied directly onto the surface of the tissue. The 6-well plates are then incubated at 37±2° C. and 5±1% CO2 for 24 hours. Thereafter, the tissue samples are washed at with 100 ml of PBS and placed into a 1.5 ml centrifuge tube containing 10-12 volumes of guanidinium thiocyanate lysis solution. The tissues are minced with fine tipped scissors and homogenized until thoroughly disrupted. After homogenization, the tissues are centrifuged at 15,000 RPM for 10 minutes. The supernatant is transferred to a new tube. The pellet (tissue debris) is discarded and the tissue homogenate is then stored at −75° C. until the RNA extraction process (described below) is completed.

RNA Isolation

RNA isolation was performed using the RNAqueous Kit from Ambion Inc. (Austin, Tex.). To the cell lysates or tissue homogenates prepared above, an equal volume of 64% ethanol is added and the tubes are vortexed. Up to 700 ml of the resulting mixture is transferred to a glass fiber filter cartridge, which is loaded into a 1.5 ml collection tube and the cartridge is centrifuged for 1 minute at 14,000 RPM. The flow-through is discarded. The remaining mixture is loaded into the filter cartridge and the centrifugation process is repeated until all of the mixture is processed. The filter is then washed to remove any residual cellular debris from the RNA bound to the glass fibers by applying 700 ml of a first wash solution (1 time) and 500 ml of a second wash solution (2 times) to the filter cartridge and centrifuging at 14,000 RPM for 1 minute to pass each wash through the cartridge. The flow-through is discarded after each wash. After the final wash, one final spin is performed without wash solution to remove any residual wash solution in the filter cartridge. The RNA bound to the glass fibers within the cartridge is then eluted by applying 30 ml of Tris-EDTA buffer (Sigma) (10 mM Tris-HCl, 1 mM EDTA (Sigma), preheated to 70-80° C., hereinbelow "TE buffer") to the cartridge and centrifuging the cartridge in a new collection tube at 14,000 RPM for one minute. For samples prepared from cell lysates and small tissues, the elution process is repeated with an additional 30 ml of preheated TE buffer. For samples prepared from larger (i.e., full thickness) tissues, the elution process is repeated two additional times. After the RNA is eluted, RNA concentration is quantified using a Ribogreen assay. RNA quality is assessed via gel electrophoresis.

RNA Concentration Assay

Ribogreen reagent (NanoDrop Technologies, Wilmington, Del.) is provided as a stock solution in DMSO. Prior to use, the reagent is diluted 2000 fold in TE buffer. The RNA assay requires 200 ml of diluted Ribogreen reagent per sample to be tested and 1 ml of reagent as a standard. Once prepared, the diluted reagent is stored protected from light. A series of RNA standards are prepared by diluting purified ribosomal RNA derived from *E. coli* to the following concentrations: 2 mg/ml, 1 mg/ml, 200 ng/ml, 40 ng/ml and 0 ng/ml (blank). Prior to assaying, the RNA samples prepared above are diluted 1000 fold in TE buffer. For the RNA assay, 100 ml of the diluted samples or standards are transferred to the wells of a black 96-well plate. The samples and standards are assayed in duplicate. After the samples/standards are added to the plate 100 ml of diluted Ribogreen assay reagent is added to the wells and the plate is gently mixed and allowed to incubate for 5-10 minutes protected from the light. After this incubation, the plate is read with a fluorometer (Cole Parmer) using an excitation wavelength of 500 nm and an emission wavelength of 525 nm.

RNA Gel Electrophoresis

A 1% RNA gel is prepared by adding 0.3 g agarose to 21.6 ml diethylpyrocarbonate (DEPC) treated water. The agarose is dissolved by boiling the water in a microwave oven. After the solution is cooled to approximately 55° C., 5.4 ml of formaldehyde and 3.0 ml 10×MOPS (3-morpholinopropanesulfonic acid) (0.2 M MOPS [pH 7.0], 20 mM sodium acetate, 10 mM EDTA, made in DEPC $H_2O$) is added and filter sterilized. After mixing, the agarose gel is cast in the horizontal gel apparatus with loading slots placed on the side of the gel closest to the negative terminal. The gel is allowed to set for at least 1 hour at room temperature. While the gel is setting, 175 ml of 1×MOPS is prepared by diluting the 10× stock. After the gel is set, the comb is removed and the buffer chamber of the gel apparatus is filled with 150-175 ml 1×MOPS (enough buffer is added to cover the gel with approximately 3 mm of buffer). The cover is placed on the apparatus, the electrical leads are attached to the power source, and the empty gel is run at 40 V (4 V/cm) for 5-10 minutes. While the gel is running, the RNA samples are prepared by transferring approximately 1 mg of each sample RNA to a 600 ml PCR tube. DEPC $H_2O$ is used to bring the total volume of all the samples to a common level and then 1-3 volumes of a gel-loading buffer (i.e. 5% glycerol, 1 mM EDTA, 0.025% bromophenol blue, 0.025% xylene cyanol FF, 20% formaldehyde, 50% formamide, 10 mg/ml ethidium bromide) are added. The samples are denatured by placing them at 65-70° C. for 5-15 minutes and then placed on ice to cool. The samples are then carefully loaded into the lanes (each loading slot can hold 10-15 ml of sample, depending upon the thickness of the gel) and run on the gel at 40 V for 1-3 hours. At the end of the run, the RNA is visualized by placing the gel on a UV transilluminator (Cleaver Scientific). An RNA sample is used for subsequent processing if both the 18S and 28S ribosomal bands are clearly visible and there is little or no staining below the 18S band.

mRNA Amplification mRNA is amplified using the MessageAmp, aRNA kit from Ambion Inc. (Austin, Tex.) as follows:

First Strand cDNA Synthesis

To start the first strand synthesis, 5 mg of total RNA for each sample are added to 600 ml PCR tubes and the total volume of liquid in the tube is adjusted to 12 ml with DEPC H2O. To each tube, 1 ml of T7 Oligo(dT) primer is added and the tube is incubated at 70±2° C. for 10 minutes to denature the RNA and is then placed on ice to allow the primer to anneal to the poly A ends of the mRNA. After cooling, 2 ml of 10× first strand buffer, 1 ml of RNAse inhibitor and 4 ml of dNTP mix is added to each tube, and the tube is placed at 42° C. As soon as the tube is heated, 1 ml of reverse transcriptase is added and the tubes are returned to 42±2° C. for 2 hours. At the end of the two hours, the tubes are briefly centrifuged to collect all of the fluid at the bottom of the tube and then placed on ice.

Second Strand Synthesis and cDNA Purification

For the synthesis of the second strand of cDNA the following ingredients are added sequentially to the tubes: 63 ml DEPC $H_2O$, 10 ml 10× second strand buffer, 4 ml dNTP mix, 2 ml DNA Polymerase and 1 ml of RNAse H. The tube is mixed and then incubated at 16±2° C. for 2 hours. Towards the end of the 2 hour incubation, a sufficient quantity of DEPC $H_2O$ is warmed to 50±2° C., and a cDNA purification filter cartridge is equilibrated with 50 ml of cDNA binding buffer (one cartridge per sample) for at least 5 minutes. After the samples are finished incubating, 250 ml of cDNA binding buffer are added to each tube and thoroughly mixed. The contents of the PCR tube are then transferred to the cDNA purification filter cartridge. The cartridge is then placed in a collection tube and centrifuged at 10,000 RPM for 1 minute. The flow-through is discarded and 650 ml of cDNA wash solution is added to the cartridge. The cartridge is centrifuged again, the flow-through is discarded, and is then centrifuged one additional time to ensure that the wash buffer has been completely emptied from the filter. The cDNA is eluted by applying 10 ml of preheated DEPC H2O to the filter and centrifuging the filter in a new collection tube at 10,000 RPM for one minute. This elution is performed one additional time to give a total volume of 16-18 ml of cDNA solution.

In Vitro Transcription to Synthesize aRNA and aRNA Purification

In vitro transcription begins by adding the following to the cDNA solution: 4 ml each of T7 ATP solution, T7 CTP solution, T7 GTP solution, T7 UTP solution, 4 ml of 10× Reaction buffer, and 4 ml of T7 enzyme mix. The tube is mixed and then incubated at 37±2° C. for 6-14 hours. Towards the end of the incubation, a sufficient volume of Elution Solution is warmed to 50-60° C. and an aRNA filter cartridge is equilibrated with 100 ml of aRNA binding buffer for at least 5 minutes. At the end of the incubation period, 350 ml of aRNA binding buffer is added to the sample tubes and thoroughly mixed. An additional 250 ml of absolute ethanol is also added to each tube. The mixture is then transferred to an aRNA filter cartridge; the cartridge is then inserted into a collection tube and centrifuged at 10,000 RPM for 1 minute. The flow-through is discarded and 650 ml of aRNA wash buffer is added to the cartridge followed by centrifuging at 10,000 RPM for one minute. After discarding the flow-through, the cartridge is spun one final time to remove all traces of the wash buffer. The cartridge is then transferred to a new collection tube. 25 ml of pre-warmed Elution Solution is added to the cartridge. The cartridge is incubated for 2 minutes at room temperature and then aRNA is eluted by centrifuging for 1 minute at 10,000 RPM. This elution is performed one additional time to give a total volume of 45-50 ml of aRNA solution. The final concentration of the aRNA is determined by the Ribogreen assay described above. In addition, the quality of the aRNA is checked via gel electrophoresis as described above. An aRNA sample is used for subsequent processing if a broad band of RNA is observed.

Labeling and Purification of aRNA aRNA is labeled with fluorescent dyes using the PerkinElmer ASAP RNA Labeling Kit. Two tubes are prepared for the labeling process—for the untreated sample Cy3 labeling (green), and for the treated sample Cy5 labeling (red). To the Cy3 tube add 2 mg of aRNA prepared from the untreated/control sample and add enough DEPC H2O to bring the total volume up to 4 ml. To the Cy5 tube add 2 mg of aRNA prepared from the sample treated with the test material and add enough DEPC H2O to bring the total volume up to 4 ml. To both tubes, add 5 ml of ASAP labeling buffer and 1 ml of the specific dye for the tube (Cy3 or Cy5). Incubate the tubes for 15 minutes at 85±2° C. At the end of the 15 minutes, place the tubes on ice to cool and then add 2.5 ml of ASAP stop solution to each tube. The above proportions are sufficient for analyzing one microarray chip. If more chips are to be used then the labeling is increased proportionately.

To purify the labeled aRNA, a microcon YM-30 filter column is inserted into a collection tube and filled with 400 ml of TE buffer. The Cy3 and Cy5 probes are combined (12.5 ml of each) and then added to the microcon filter and thoroughly mixed with the TE buffer. The filter is centrifuged at 12,000 RPM for 8 minutes and the flow-through is discarded. The column is washed twice with 400 ml of TE buffer, discarding the flow though each time. After the final wash, the filter column is inverted, placed into a new collection tube and centrifuged at 12,000 RPM for 2 minutes to collect the probe (the probe is concentrated in a volume of 2-30 ml of residual TE buffer).

Microarray Hybridization and Washing

For hybridization, 45 ml of 10× control target RNA (supplied with Agilent Technologies In Situ Hybridization Kit) is mixed with 160 ml of DEPC $H_2O$ and 9 ml of 25× Agilent Fragmentation Buffer. This mixture is incubated at 60° C. for approximately 30 minutes in a hybridization oven. At the end of the incubation, 225 ml of Agilent Hybridization Buffer is added along with the fluorescent aRNA probes prepared above. The mixture is then incubated at 70° C. for 5-10 minutes in a waterbath. During this incubation period, an Agilent SUREHYB hybridization chamber is prepared by inserting a glass gasket slide into the bottom half of the chamber. At then end of the incubation, the hybridization mixture (approximately 450 ml) is applied to the glass gasket slide and an Agilent Human 1A Oligo Microarray Chip is placed face down on top of the gasket such that the hybridization solution is sandwiched between the glass gasket slide and the microarray face of the chip. The top half of the chamber is attached and the connecting thumbscrew tightened. After verifying that there is good bubble formation in the chamber, it is placed into the hybridization oven for approximately 17 hours (60° C. and rotating at 4 RPM). At then end of the hybridization period, the microarray/glass gasket is removed from the SUREHYB chamber and placed in 50 ml of a first wash solution (room temperature, 6×SSC, 0.005% Triton X-102). After the gasket has fallen away from the microarray, the array is transferred to 300 ml of fresh wash solution 1 on a magnetic stir plate. The array is washed while the solution is mixed at medium speed for 10 minutes and is then transferred to 300 ml of wash solution 2 (0.1×SSX, 0.005% Triton X-102, 4° C.) for 5 minutes. After the final wash, the array is centrifuged at 500 RPM for 5 minutes until dry.

Microarray Scanning and Analysis

The microarrays are scanned with an Axon GenePix 4100A Scanner with the scanning resolution set to 10 mm and analyzed with GenePix Pro software. During the initial scan the PMT gains for the scanner are adjusted such that the Cy5/Cy3 image count ratios are between 0.88 and 1.12.

To derive the standard curve for the Ribogreen assay, the relative fluorescent units (RFU) versus the known RNA concentrations in mg/ml for the standards is plotted and subjected to regression analysis to establish the line that best fits these data points. Mean RFU values for the test materials and untreated samples are then used to estimate the amount of RNA present in each sample. The level of gene expression is related to the fluorescence intensity of the probed gene marker on the microarray. Fluorescence measurements between the Cy3 and Cy5 probes are normalized. The total fluorescent signal for both dyes is normalized with a correction factor such that the ratio of total intensities for both dyes equal to one.

Criteria for evaluating changes in gene expression are known to those of ordinary skill in the art and include the following: (i) the ratio of Cy3/Cy5 (untreated/treated) fluorescence intensity is greater than 1.5 or less than 0.66, corresponding to a change in gene expression of at least +/−30%; (ii) the fluorescence intensity of the gene marker is greater than the background intensity; (iii) the gene feature is clearly marked specifically by the aRNA probes and is not due to non-specific fluorescence. The first two criteria are filtered via computer analysis. The last criterion requires visual inspection of the array.

Cy3/Cy5 ratios of greater than about 1.3 are interpreted to indicate that a gene is upregulated by the treatment, whereas ratios of less than about 0.7 are interpreted to indicate a downregulated gene. Thus, a ratio of 1.3, where the treated value is 130% of the untreated value, indicates a 30% increase in gene expression. Similarly, a ratio of 0.7 means that the treated value was 70% of the untreated value, indicating a 30% decrease in gene expression.

EXAMPLE 1

Two polysaccharopeptide extracts of—the first, a hydrolyzed with acid protease of *R. miehei* and thereafter rendered substantially devoid of acid protease activity according to the methods described above, the second a non-hydrolyzed extract—were tested for the ability to increase the level of expression of GLO-1. The acid protease hydrolyzed extract increased the expression of mRNA coding for GLO-1 by about 50%.

Anti-AGE compositions according to the present invention may optionally include (in addition to extract of *G. lucidum* hydrolyzed with acid protease of *R. miehei* and thereafter rendered substantially devoid of acid protease activity) one or more anti-AGE compounds known to those of ordinary skill in the art, including amino guanidine and carnosine.

Anti-AGE compositions according to the present invention may also optionally include one or more steroidal or non-steroidal anti-inflammatory drug (NSAID) known to those of ordinary skill in the art. Preferred examples of NSAIDS include propionic acid derivatives, acetic acid derivatives, fenamic acid derivatives, biphenylcarboxylic acid derivatives, and oxicams.

In a further embodiment of the present invention, Anti-AGE compositions according to the present invention may also optionally include one or more photoprotective agents selected from the group consisting of inorganic sunblock pigments, preferably Zinc oxide or Titanium dioxide, and organic sunscreen active agents. The latter includes, but is not limited to, p-Aminobenzoic acid (PABA) up to 15%; Avobenzone up to 3%; Cinoxate up to 3%; Dioxybenzone up to 3%; Homosalate up to 15%; Menthyl anthranilate up to 5%; Octocrylene up to 10%; Octyl methoxycinnamate (Octinoxate) up to 7.5%; Octyl salicylate up to 5%; Oxybenzone up to 6%; Padimate O up to 8%; Phenylbenzimidazole sulfonic acid (Ensulizole) up to 4%; Sulisobenzone up to 10%; Trolamine salicylate up to 12%. Other organic sunscreen active ingredients accepted for use in products intended to contact human skin that are approved in countries outside the US are also considered to be within the scope of the present invention.

Another embodiment of the present invention is directed to anti-AGE compositions containing an extract of *G. lucidum* hydrolyzed with acid protease of *R. miehei* and thereafter rendered substantially devoid of acid protease activity in combination with at least one antioxidant. Preferred antioxidants include, but are not limited to the following: retinoids selected from the group consisting of retinol, retinal, retinol esters, retinyl propionate, retinoic acid, retinyl palmitate; ascorbic acid, derivatives of ascorbic acid and mixtures thereof; tocopherol, derivatives of tocopherol and mixtures thereof.

The Cosmetic, Toiletries & Fragrance Association, *International Cosmetic Ingredient Dictionary and Handbook*, Vol. II, p. 1364 (11th Edition, 2006) ("CTFA Dictionary") describes a wide variety of non-limiting cosmetic and pharmaceutical ingredients commonly used in the skin care industry, which are also suitable for use in combination with the extract of *G. lucidum* hydrolyzed with acid protease of *R. miehei* and thereafter rendered substantially devoid of acid protease activity as claimed in the present application.

EXAMPLE 2

Inhibition of AGE-related proteins was assayed according to the following method. First, a reaction mixture was prepared by mixing 20 mg/ml of human serum albumin (HSA) in 200 mM phosphate buffer (pH 7.4) with 500 mM [90.08 mg/ml] of glucose and 0.02% [0.2 mg/ml] sodium azide (as a preservative). The reaction mixture was incubated at 37° C. for three weeks, during which time AGE-related proteins were produced via a Maillard-type reaction. After 7, 14 and 21 days, aliquots of the reaction mixture were passed through a molecular weight sieve (PD-10 column) and equilibrated in water to remove free glucose and Schiff base. AGE-related proteins in the reaction mixture were assayed by diluting and incubating samples with 12 mg/ml NalO$_4$ at room temperature for 30 minutes, followed by addition of 15% (150 mg/ml) ZnSO$_4$ and 0.7M (28 mg/ml) NaOH to quench any unreacted NalO$_4$. Samples were centrifuged to eliminate precipitates. The supernatant was the incubated with a 1/10 dilution of acetylacetone [2,4-pentanedione] in 3.3M [254.4 mg/ml] ammonium acetate. The latter reaction generates fluorescent by-products with fluorescence proportional to the amount of accumulated AGE-related proteins as determined with a microplate fluorescence reader (Bio-Tek FL600) at an excitation wavelength of 360 nm and an emission wavelength of 440 nm.

| Test Method Validation | | |
| --- | --- | --- |
| HSA (20 mg/ml) + phosphate buffer + sodium azide (0.02%) | 7 days | 0.045 |
| glucose (500 mM) + phosphate buffer + sodium azide (0.02%) | 7 days | 0.034 |
| HSA (20 mg/ml) + glucose (500 mM) + phosphate buffer + sodium azide (0.02%) | 7 days | 0.654 |
| HSA (20 mg/ml) + glucose (500 mM) + phosphate buffer + sodium azide (0.02%) | 14 days | 0.789 |
| HSA (20 mg/ml) + glucose (500 mM) + phosphate buffer + sodium azide (0.02%) | 21 days | 0.832 |

To aliquots of the initial reaction mixture capable of producing AGE-related endproducts as described above were added varying concentrations of extract of *G. lucidum* according to the present invention (i.e., hydrolyzed with acid protease of *R. miehei* and thereafter rendered substantially devoid of acid protease activity). In the following table, extract of *G. lucidum* according to the present invention is referenced by its tradename, ACTIAGE™. Aminoguanidine, a known antiglycation agent, was also added to the reaction mixture as a positive control. Fluorescence was measured after 7 days of incubation in the reaction mixture as set out above.

| Inhibition of AGE-Related Products | Fluorescence (at 440 nm)* |
| --- | --- |
| Positive Control - HSA (20 mg/ml) + glucose (500 mM) + phosphate buffer + sodium azide (0.02%) | 100 |
| Negative Control - glucose (500 mM) + phosphate buffer + sodium azide (0.02%) | 08 |

-continued

| Inhibition of AGE-Related Products | Fluorescence (at 440 nm)* |
| --- | --- |
| 100 mM aminoguanidine + Positive Control | 73 |
| 200 mM aminoguanidine + Positive Control | 45 |
| 0.01% ACTIAGE ™ | 95 |
| 0.1% ACTIAGE ™ | 76 |
| 1.0% ACTIAGE ™ | 53 |
| 1.0% ACTIAGE ™ + Positive Control | 38 |
| 10.0% ACTIAGE ™ | 45 |
| 10.0% ACTIAGE ™ + Positive Control | 31 |

*normalized to 100; actual fluorescence = 0.705

The following formulation examples are further illustrative of the present invention. The components and specific ingredients are presented as being typical, and various modifications can be derived in view of the foregoing disclosure within the scope of the invention. All percentages, ratios and proportions herein are by weight, unless otherwise specified. All temperatures are in degrees Celsius unless otherwise specified.

FORMULATION EXAMPLE 1

Toner

| | |
| --- | --- |
| Deionized Water | 93.190% |
| Methyl Gluceth-20 | 1.000% |
| Potassium Sorbate | 0.100% |
| Sodium Benzoate | 0.100% |
| Phenoxyethanol | 0.600% |
| Citric acid | 0.010% |
| Extract of *G. lucidum* hydrolyzed with acid protease of *R. miehei* and thereafter rendered substantially devoid of acid protease activity | 5.000% |

Add ingredients sequentially in order listed. Mix until clear. End processing.

FORMULATION EXAMPLE 2

Face Cream

| | |
| --- | --- |
| Part A | |
| Deionized Water | 62.600% |
| Magnesium Aluminum Silicate | 0.400% |
| Xanthan Gum | 0.150% |
| Acrylates/C$_{10-30}$ Alkyl Acrylate Crosspolymer | 0.750% |
| Part B | |
| Butylene Glycol | 4.000% |
| Disodium EDTA | 0.050% |
| Part C | |
| Hydrogenated Lecithin | 0.500% |
| Caprylic/Capric Triglyceride | 8.000% |
| *Simmondsia Chinensis* (Jojoba) Seed Oil | 5.000% |
| Octyl Palmitate | 4.000% |
| Cetearyl Alcohol | 2.000% |
| PEG-8 Stearate | 1.000% |
| PEG-100 Stearate | 0.800% |

-continued

| Part D | |
|---|---|
| Triethanolamine 99% | 0.100% |
| Part E | |
| *Aloe Barbadensis* Leaf Juice (Activera ® 10x, Active Organics) | 5.000% |
| Phenoxyethanol | 0.500% |
| Potassium Sorbate | 0.100% |
| Methylisothiazolinone | 0.050% |
| Extract of *G. lucidum* hydrolyzed with acid protease of *R. miehei* and thereafter rendered substantially devoid of acid protease activity | 5.000% |

Sprinkle Magnesium Aluminum Silicate, Xanthan Gum, Acrylates/$C_{10-30}$ Alkyl Acrylate Crosspolymer into vortex of water. Mix and heat to 80° C. Add Part B to Part A, mix and hold the temperature at 80° C. In a separate vessel, mix Part C and heat to 75° C., mix until clear. Add Part C to Parts A and B, mix for 10 minutes. Add Part D to Parts ABC. Mix for 15 minutes. Switch to sweep mixing. Cool batch to 45° C. In a separate container, add ingredients in Part E. Mix until uniform. At 45° C., add Part E, to Parts ABCD. Mix and cool to 25° C. End processing.

FORMULATION EXAMPLE 3

Eye Cream

| Part A | |
|---|---|
| Deionized Water | 57.650% |
| Acrylates/C10-30 Alkyl Acrylate Crosspolymer | 0.300% |
| Panthenol | 0.100% |
| Potassium Sorbate | 0.100% |
| Disodium EDTA | 0.100% |
| Allantoin | 0.100% |
| Part B | |
| Caprylic/Capric Triglyceride | 2.000% |
| Dimethicone | 3.000% |
| *Butyrospermum Parkii* (Shea Butter) | 2.000% |
| *Carthamus Tinctorius* (Safflower) Seed Oil | 2.000% |
| Cetearyl Alcohol | 1.500% |
| Dimethiconol | 1.300% |
| Steareth-2 | 1.000% |
| Steareth-21 | 0.500% |
| Cyclomethicone | 5.000% |
| Part C | |
| Triethanolamine | 0.250% |
| Part D | |
| Carbomer 940 2% Solution | 10.000% |
| Part E | |
| *Mucor Miehei* Extract, Butylene Glycol, and N-Acetylglucosamine | 5.000% |
| Part F | |
| Sodium Hyaluronate (Actimoist ® Bio 2, Active Organics) | 2.000% |
| Phenonip | 1.000% |
| *Aloe Barbadensis* Leaf Juice (Activera ® 10X, Active Organics) | 5.000% |
| Tocopherol | 0.100% |

Sprinkle Acrylates/$C_{10-30}$ Alkyl Acrylate Crosspolymer into vortex of water. Mix and heat to 75° C. Mix and heat Part B to 70° C. Add Part B to Part A, mix for 10 minutes. Add Part C. Mix for 10 minutes. Add Part D. Mix and cool to 45° C. At 45° C., add Parts E and F. Mix and cool to 25° C. End processing.

FORMULATION EXAMPLE 4

Lipstick

| Part A | |
|---|---|
| *Ricinus Communis* (Castor) Seed Oil | 24.37% |
| Octyl Palmitate | 33.33% |
| Petrolatum | 10.84% |
| Beeswax | 3.33% |
| Paraffin Wax | 3.33% |
| *Euphorbia Cerifera* (Candelilla) Wax | 5.20% |
| Ozokerite | 3.00% |
| *Copernicia Cerifera* (Carnauba) Wax | 2.50% |
| *Simmondsia Chinensis* (Jojoba) Seed Oil | 8.00% |
| Propylparaben | 0.10% |
| Part B | |
| Polyglyceryl-4 Isostearate | 1.00% |
| *Mucor Miehei* Extract, Butylene Glycol, and N-Acetylglucosamine | 5.00% |

Mix and heat Part A to 80° C. Pre-mix Part B; add to Part A. Mix and pour into container.

FORMULATION EXAMPLE 5

Face Mask

| Part A | |
|---|---|
| Deionized Water | 59.960% |
| Aloe Barbadensis Leaf Juice (Activera ™ 10X, Active Organics) | 5.000% |
| Glycerin | 4.000% |
| Caffeine | 0.100% |
| Acacia Gum | 0.300% |
| Chromium Oxide Green | 0.500% |
| Titanium Dioxide | 3.000% |
| Methylparaben | 0.200% |
| Part B | |
| Glyceryl Stearate | 6.000% |
| *Simmondsia Chinensis* (Jojoba) Seed Oil | 1.500% |
| Tocopheryl Acetate | 0.100% |
| Propylparaben | 0.100% |
| Part C | |
| Bentonite | 11.000% |
| Part D | |
| Phenoxyethanol | 0.500% |
| Citric Acid 50% | 2.100% |
| Extract of G. lucidum hydrolyzed with acid protease of R. miehei and thereafter rendered substantially devoid of acid protease activity | 5.000% |
| Part E | |
| Essential Oil (Spearmint) | 0.070% |
| Essential Oil (Peppermint) | 0.070% |

Mix and heat Part A to 75° C. Mix and heat Part B to 75° C. Homogenize Part A, then add Part B continuing, mixing in the homogenizer for 5 minutes. Start to cool. At 60° C., add Part C; mix well. Continue cooling. At 45° C., add Parts D and E. Mix and cool to 25° C. End processing.

FORMULATION EXAMPLE 6

Moisturizing Shampoo

| Part A | |
|---|---|
| Deionized Water | 46.680% |
| *Aloe Barbadensis* Leaf Juice (Activera ® 10X, Active Organics) | 10.000% |
| Part B | |
| Sodium C14-16 Olefin Sulfonate | 18.000% |
| Cocamidopropyl Betaine | 18.000% |
| Glucamate DOE-120 | 1.000% |
| Part C | |
| Phenoxyethanol | 0.300% |
| Kathon CG | 0.020% |
| Sodium Chloride 25% Solution | qs |
| Butylene Glycol and *Spiraea Ulmaria* Extract (Actiphyte ® Queen of Meadow Concentrate, Active Organics) | 1.000% |
| Part D | |
| Extract of *G. lucidum* hydrolyzed with acid protease of *R. miehei* and thereafter rendered substantially devoid of acid protease activity | 5.000% |

Mix and heat Part A to 50° C. Add Part B to Part A; mix until clear. Add Parts C and D to Parts A and B. Mix and cool to 25° C. End processing.

FORMULATION EXAMPLE 7

Moisturizing Conditioner

| Part A | |
|---|---|
| Deionized Water | 64.670% |
| *Aloe Barbadensis* Leaf Juice (Activera ® 10X, Active Organics) | 5.000% |
| Panthenol | 0.200% |
| Part B | |
| Jojoba Oil | 2.000% |
| Behentrimonium Methosulfate, Cetearyl Alcohol | 4.000% |
| Stearamidopropyl Dimethylamine | 2.000% |
| Cetearyl Alcohol | 4.500% |
| PEG-100 Stearate | 0.880% |
| Glyceryl Stearate | 1.200% |
| Part C | |
| Water, Phenyl Trimethicone, Cyclomethicone, Polysilicone-11, Lecithin (Actiprime ™ 100, Active Organics) | 10.000% |
| Part D | |
| Extract of *G. lucidum* hydrolyzed with acid protease of *R. miehei* and thereafter rendered substantially devoid of acid protease activity | 5.000% |
| Phenoxyethanol | 0.500% |
| Methylisothiazolinone | 0.050% |

Mix and heat Part A to 75° C. Mix and heat Part B to 75° C. Add Part B to Part A. After mixing, add Part C and mix. Cool until 45° C., the add Part D. Mix and cool to 25° C. End processing.

FORMULATION EXAMPLE 8

Face Serum

| Part A | |
|---|---|
| Deionized Water | 80.850% |
| Keltrol RD | 0.250% |
| Butylene Glycol | 0.400% |
| Part B | |
| Water | 0.600% |
| Potassium Sorbate | 0.100% |
| Part C | |
| Water, Algae Extract, and *Aloe Barbadensis* Leaf Juice (Actisea ® 100, Active Organics) | 5.0% |
| Part D | |
| *Aloe Barbadensis* Leaf Juice (Activera ® 10x, Active Organics) | 5.000% |
| Phenoxyethanol | 0.600% |
| Neolone 950 | 0.050% |
| Extract of *G. lucidum* hydrolyzed with acid protease of *R. miehei* and thereafter rendered substantially devoid of acid protease activity | 5.000% |
| Part E | |
| Water | 2.000% |
| Allantoin | 0.1% |
| Disodium EDTA | 0.05% |

Mix Part A. Add pre-dissolved Part B; mix until uniform. Add Part C; mix until uniform. Add Part D; mix well. Add pre-dissolved Part E, mix until uniform. End processing.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A topical anti-AGE mushroom hydrolysate substantially devoid of acid protease activity produced by the steps of (a) extracting the water-soluble polysaccharopeptide constituents of *Ganoderma lucidum* in an acidic aqueous solvent having a pH of from about 3.5 to about 4.5 (b) hydrolysis of the resultant water-soluble polysaccharopeptide extract with an acid protease enzyme of *Rhizomucor miehei* and (c) inactivation or removal of the acid protease via molecular weight sieve, thermal inactivation and/or pepstatin-affinity gel chromatography.

2. A method for inhibiting the formation of AGE related protein comprising applying to the skin of a mammal a therapeutically-effective amount of a topical anti-AGE mushroom hydrolysate according to claim 1.

3. The method of claim 2, where the topical anti-AGE mushroom hydrolysate of claim 1 is applied in a concentration sufficient to increase the expression of mRNA coding for GLO-1 by at least about 33%.

4. The method of claim 2, where the topical anti-AGE mushroom hydrolysate of claim 1 is applied in a concentration sufficient to increase the expression of mRNA coding for GLO-1 by at least about 40%.

5. The method of claim 2, where the topical anti-AGE mushroom hydrolysate of claim 1 is applied in a concentration sufficient to increase the expression of mRNA coding for GLO-1 by at least about 50%.

6. A topical anti-AGE mushroom hydrolysate substantially devoid of acid protease activity according to claim 1 wherein the acid protease enzyme of *Rhizomucor miehei* used to hydrolyze the water-soluble polysaccharopeptide extract of *Ganoderma lucidum* has from about 4,000 to about 10,000 HUT units of activity per milliliter.

7. A dermatocosmetic composition comprising from about 0.01% to about 10% by weight of a topical anti-AGE mushroom hydrolysate according to claim 1.

8. A dermatocosmetic composition of claim 7 further comprising at least one additional topical anti-AGE agent.

9. A dermatocosmetic composition of claim 7 wherein the at least one additional topical anti-AGE agent is selected from the group consisting of amino guanidine and carnosine.

10. A dermatocosmetic composition of claim 7 further comprising at least one of a photoprotective agent, an antioxidant.

* * * * *